United States Patent [19]
Normansell et al.

[11] Patent Number: 6,037,156
[45] Date of Patent: *Mar. 14, 2000

[54] DNA MOLECULES AND VECTORS ENCODING CLAVULANIC ACID BIOSYNTHESIS ENZYMES

[75] Inventors: Ian D. Normansell; John E. Hodgson; Alison J. Earl, all of Brentford, United Kingdom

[73] Assignee: Beecham Group p.l.c., Brentford, United Kingdom

[*] Notice: This patent is subject to a terminal disclaimer.

[21] Appl. No.: 09/036,738

[22] Filed: Mar. 9, 1998

Related U.S. Application Data

[62] Division of application No. 08/159,950, Dec. 1, 1993, Pat. No. 5,759,831, which is a continuation of application No. 07/921,352, Jul. 24, 1992, abandoned, which is a continuation of application No. 07/664,460, Mar. 1, 1991, abandoned, which is a continuation of application No. 07/358,671, May 30, 1989, abandoned.

[51] Int. Cl.$^7$ .......................... C12N 15/74; C12N 15/00; C07H 21/04; C12Q 1/68
[52] U.S. Cl. ................. 435/183; 435/252.3; 435/252.33; 435/252.35; 435/320.1; 435/375; 435/471; 435/476; 435/6; 536/23.2; 536/23.7
[58] Field of Search ............................ 435/183, 6, 320.1, 435/440, 252.35, 252.33, 375, 476, 471; 536/23.2, 23.7

[56] References Cited

FOREIGN PATENT DOCUMENTS 0233715  8/1987  European Pat. Off. .
0349121  1/1990  European Pat. Off. .

OTHER PUBLICATIONS

Communication of Notice of Opposition from European Patent Office, including Facts and Arguments, against EP 0 349 121 B1 (Ref. AE herein) by Biochemie GmbH.

F. Malpartida and D.A. Hopwood, "Molecular cloning of the whole biosynthetic pathway of a Streptomyces antibiotic . . . ," *Nature*, vol. 309, 462–4 (May 31, 1984).

C.R. Bailey et al., "Cloning a *Streptomyces clavuligerus* genetic locus involved in clavulanic acid biosynthesis," *Bio/Technology*, Sep. 1984, 808–811.

J. Romero et al., "Isolation and biochemical characterization of *Streptomyces clavuligerus* mutants in the biosynthesis . . . ," *Appl. Microbiol. Biotechnol*, 1988, 27:510–516.

J. Romero et al., "Dissociation of cephamycin and clavulanic acid biosynthesis . . . ," *Appl. Microbiol. Biotechnol.*, 1984, 20:318–325.

ATCC Catalogue of Bacteria, Phages & rDNA Vectors, 16$^{th}$ ed., 1985, p. 181.

*Primary Examiner*—John L. LeGuyader
*Attorney, Agent, or Firm*—Zoltan Kerekes; Stephen Venetianer; Charles M. Kinzig

[57] ABSTRACT

DNA sequences obtained from *S. clavuligerus*, recombinant vectors incorporating such sequences and hosts transformed with such vectors are disclosed. The DNA comprises one or more genes encoding one or more enzymes involved in the biosynthesis of clavulanic acid and may be used to improve the yield of clavulanic acid produced by clavulanic acid–producing organisms such as *S. clavuligerus* ATCC 27064.

23 Claims, 6 Drawing Sheets

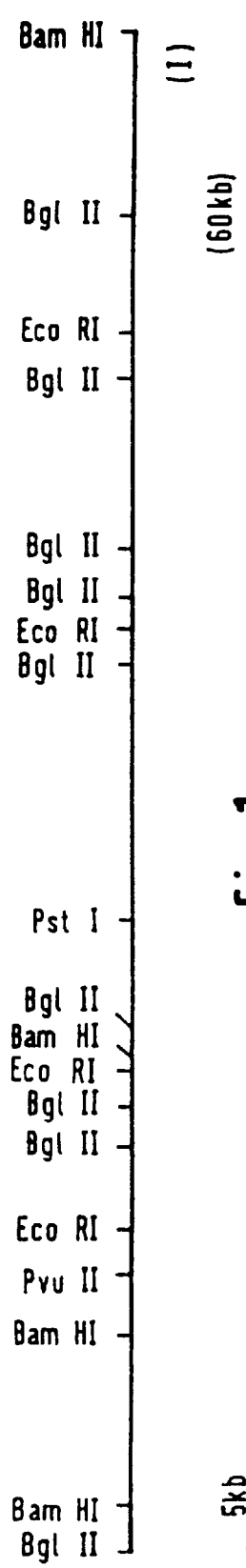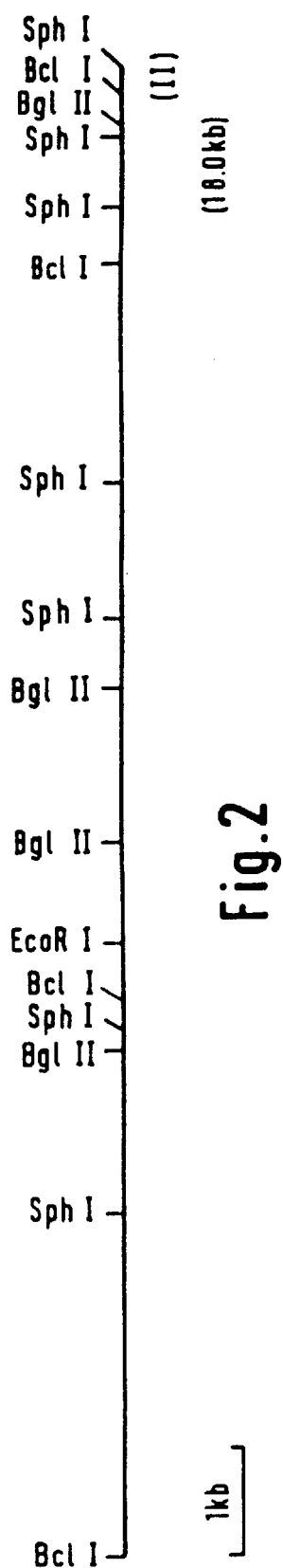

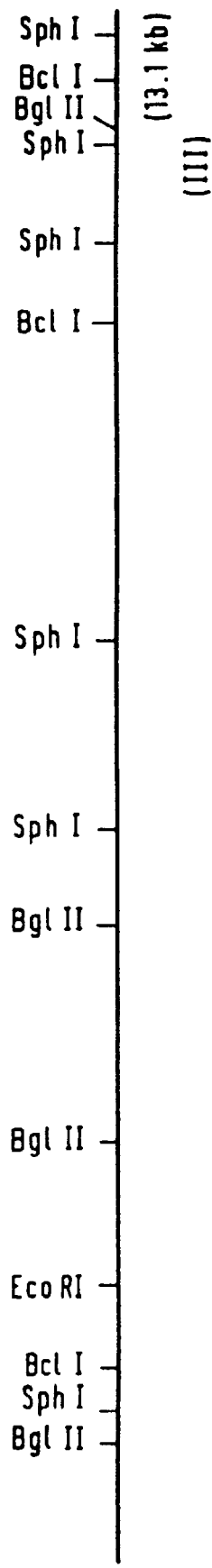

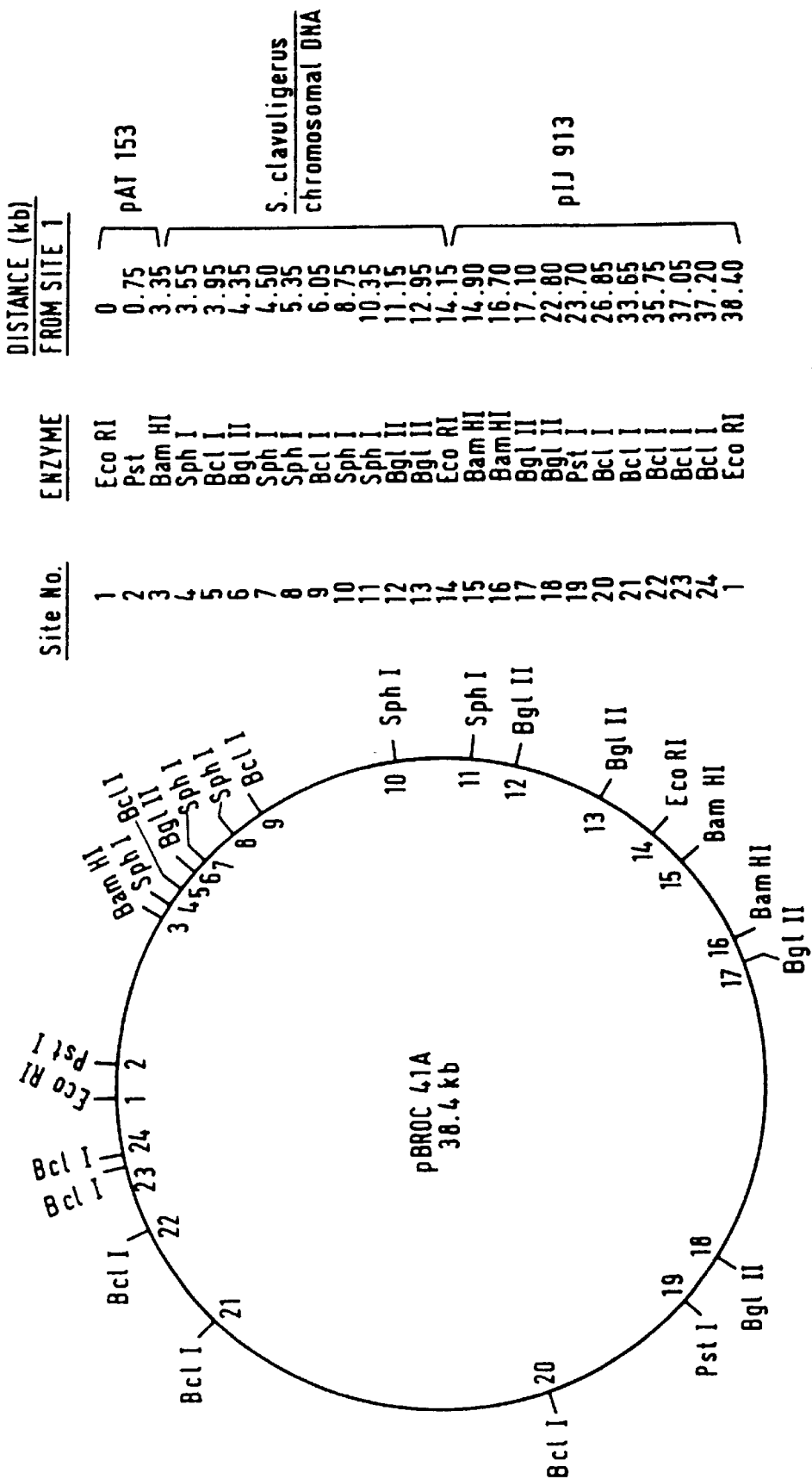
Fig. 5a Restriction Map of pBROC 41A

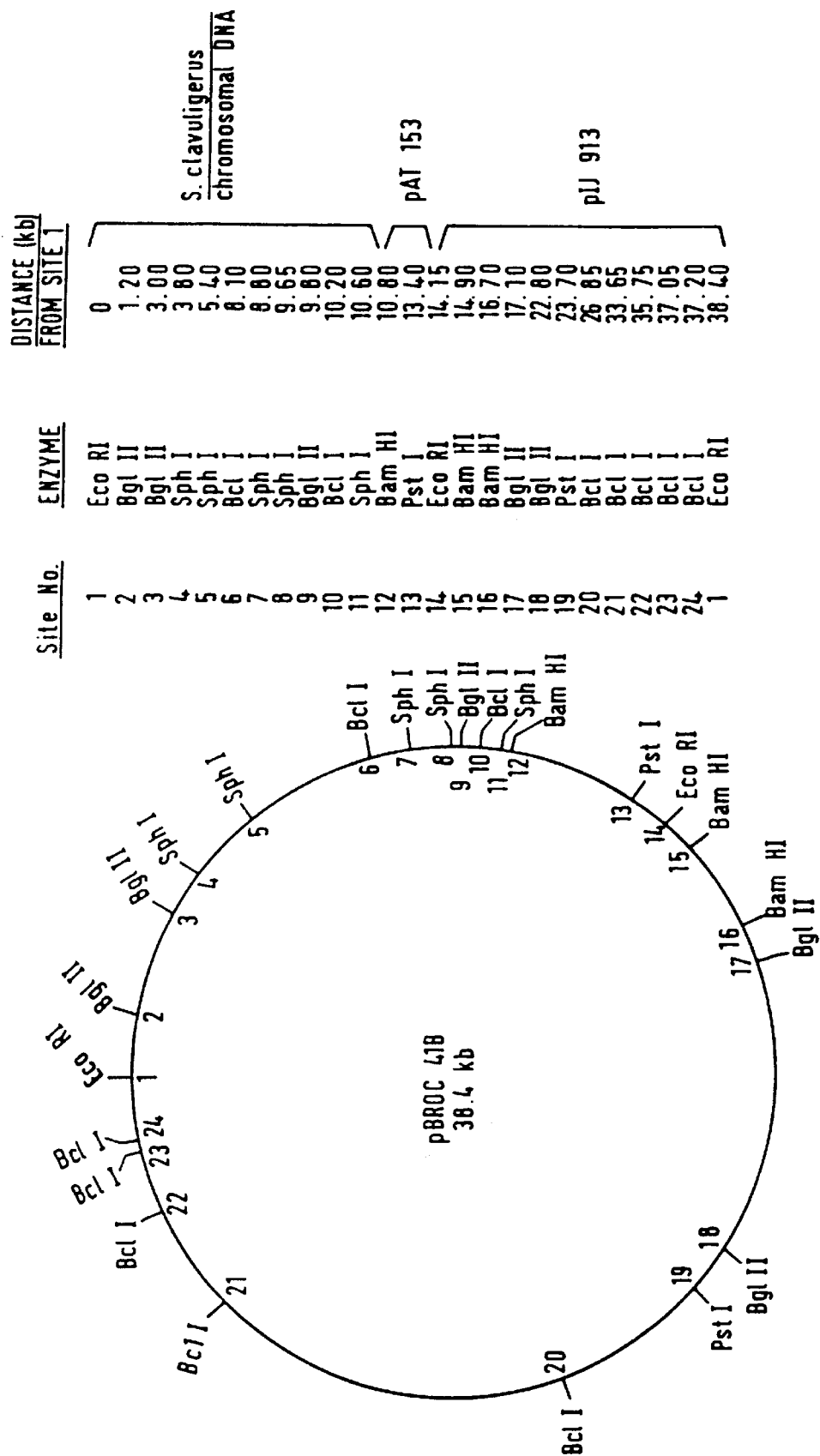
Fig. 5b  Restriction Map of pBROC 41B

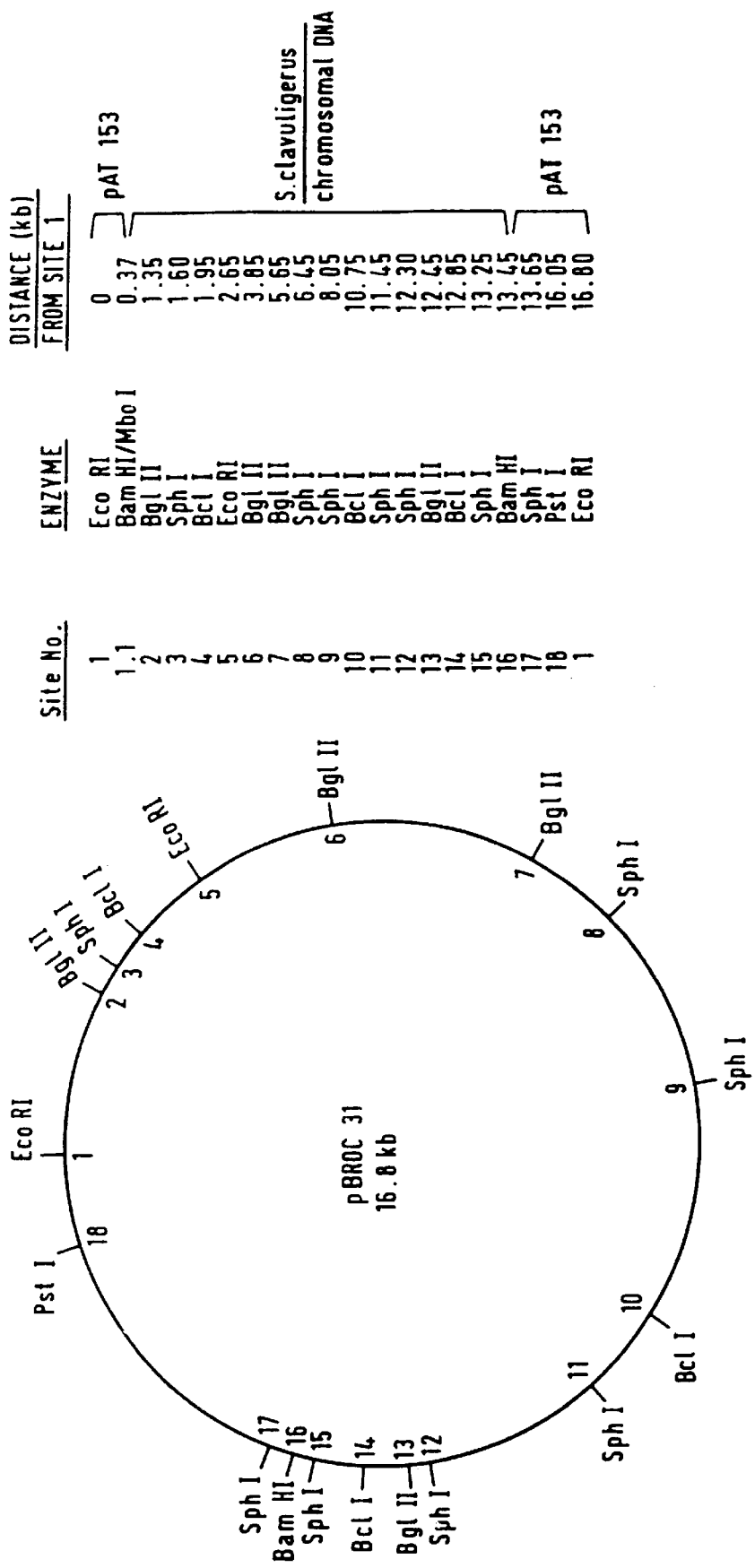
Fig. 6 Restriction Map of pBROC 31

DNA MOLECULES AND VECTORS ENCODING CLAVULANIC ACID BIOSYNTHESIS ENZYMES

This application is a division of application Ser. No. 159,950, filed Dec. 1, 1993, now U.S. Pat. No. 5,759,831, which is a continuation of application Ser. No. 921,352, filed Jul. 24, 1992, now abandoned, which is a continuation of application Ser. No. 664,460, filed Mar. 1, 1991, now abandoned, which is a continuation of application Ser. No. 358,671, filed May 30, 1989, now abandoned.

The present invention relates to DNA molecules especially recombinant DNA molecules, and in particular to recombinant vectors for use in the transformation of a microbial host which contain inserted DNA fragments carrying one or more genes coding for enzymes involved in clavulanic acid biosynthesis.

Clavulanic acid is a potent β-lactamase inhibitor produced by the mycelial bacterium *Streptomyces clavuligerus* (see Reading, C., and Cole, M., Antimicrobial Agents and Chemotherapy, 1977, 11, 852–857) and is a compound of great clinical value, since it protects β-lactamase-labile β-lactam antibiotics from degradation. Methods for increasing the yield (titre) of clavulanic acid in fermentation processes are potentially, therefore, of considerable commercial importance.

One approach to the problem of clavulanic acid yield improvement that has been envisaged involves the use of recombinant DNA techniques using *S. clavuligerus* as the host cell. In this connection, it was suggested that isolation of genes involved in clavulanic acid biosynthesis from the chromosomal DNA of *S. clavuligerus* would be a possible starting point (see C. R. Bailey et al, *Biotechnology*, 1984, 2, 808–811). Hitherto, however, no DNA has been specifically identified as being of value for increasing clavulanic acid titre.

Although several enzymes are believed to be involved in clavulanic acid biosynthesis, only the enzyme clavulanic acid synthase (or synthetase) has so far been characterised. Clavaminic acid synthase (hereinafter abbreviated to CAS) is a 2-oxoglutarate linked oxygenase which converts proclavaminic acid into clavaminic acid (these are intermediates in the clavulanic acid biosynthetic pathway). For further details see papers by S. W. Elson et al in *J. Chem. Soc. Chem. Commun.*, 1987, pages 1736, 1738, and 1739. See also European Patent Application Publication No. 0 213 914.

In order to clearly define the invention reference is made to the accompanying drawings in which:

FIG. 1 is a restriction map of DNA I

FIG. 2 is a restriction map of DNA II

FIG. 3 is a restriction map of DNA III

FIG. 5a is a restriction map of the recombinant plasmid pBROC 41A;

FIG. 5b is a restriction map of the recombinant plasmid pBROC 41B; and

FIG. 6 is a restriction map of the recombinant plasmid pBROC 31.

Figure 4:
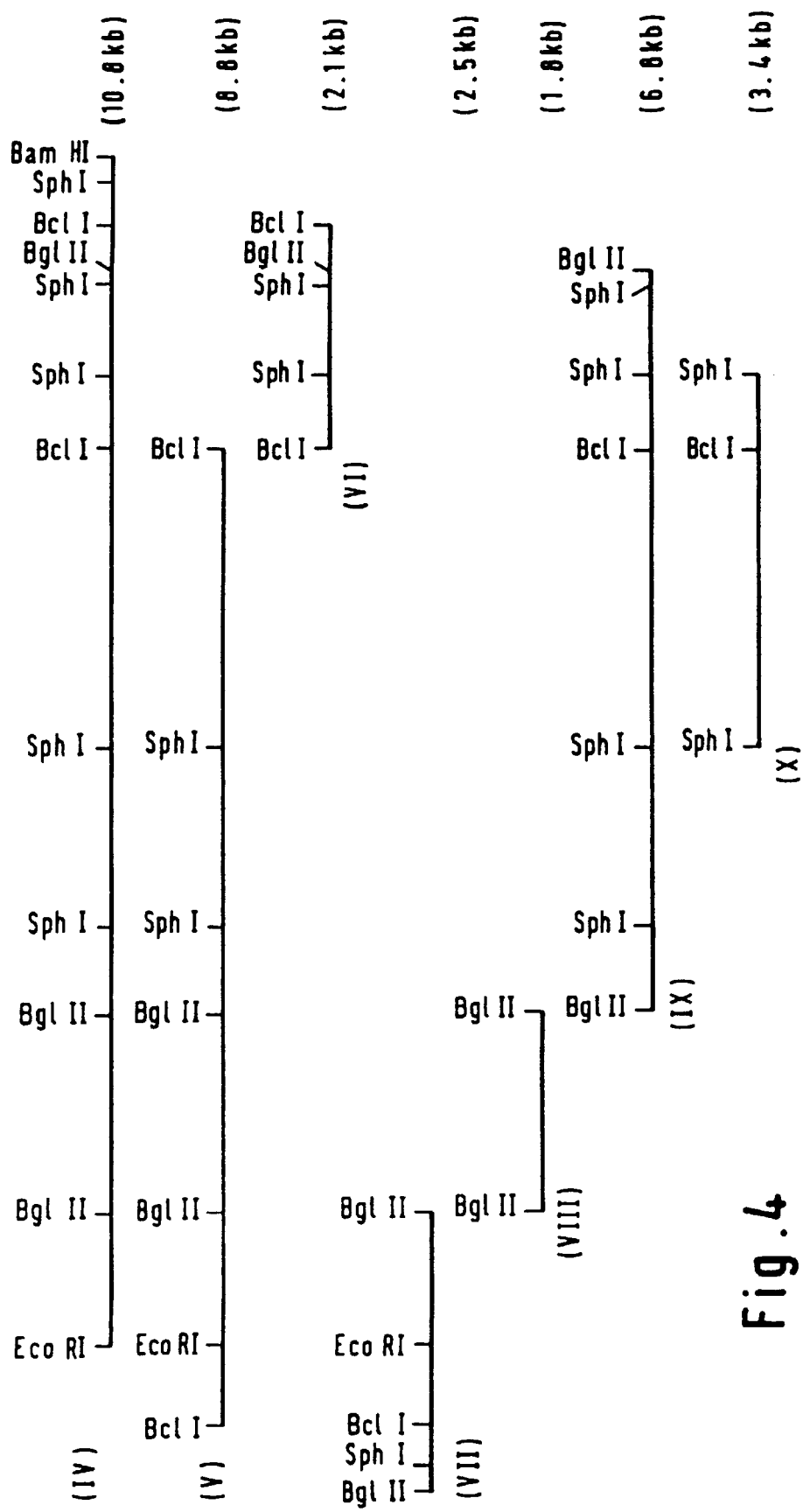
FIG. 4 is a restriction map of seven restriction fragments derived from DNA III

In the Figures the abbreviations Eco RI, Pst I etc. are conventional abbreviations for restriction endonucleases, and the approximate length in kilobases (Kb) of the DNA, as determined by sizing experiments carried out by agarose gel electrophoresis, is indicated. It should be understood that the Figures restriction sites present on the DNA fragments illustrated.

In a first aspect, the present invnetion provides DNA comprising a sequence which encodes at least one enzyme involved in clavulanic acid biosynthesis, characterised in that the DNA is approximately 60 kb in length and has the configuration of restriction sites shown in DNA fragment (I) in FIG. 1.

It will be appreciated that the DNA (I) of the invention is not in its 'natural' state (i.e. as found in the chromosomal DNA of *S. clavuligerus*) but has been purified and isolated to separate it form flanking DNA.

The advantage of the invention is that DNA (I) comprises one or more genes involved in clavulanic acid biosynthesis which can be utilised, as hereinbelow described, to increase the yield of clavulanic acid produced by a clavulanic acid producing organism. A particular advantage is that the titre of clavulanic acid can be substantially increased in wild-type Streptomyces species, for example *S. clavuligerus* ATCC 27064, which naturally tend to produced only fairly low levels of clavulanic acid.

Certain restriction fragments of the DNA (I) may also be utilised in the above manner provided they contain one or more intact genes involved in clavulanic acid biosynthesis.

Accordingly, the present invention further provides DNA which is a subfragment of the DNA (I) shown in FIG. 1, with the proviso that if the subfragment is a subfragment of the DNA (II) shown in FIG. 2, the subfragment is identical with or is a subfragment of the DNA (III) shown in FIG. 3.

The subfragment according to the invention may be derived by cleaving the DNA (I) with appropriate restriction enzymes by known methods. Subfragments according to the invention may also be prepared by cleaving larger DNA subfragments with appropriate restriction enzymes or by ligating smaller subfragments using known methods.

A preferred subfragment has the configuration of restriction sites shown in DNA (III) in FIG. 3 or is a subfragment thereof.

Particular subfragments of the DNA (III) include those shown in FIG. 4, viz:

a) EcoRI—BamHI fragment (IV);

b) BclI—BclI fragment (V);

c) BclI—BclI fragment (VI);

d) BglII—BglII fragment (VII);

e) BglII—BglII fragment (VIII);

f) BglII—BglII fragment (IX);

g) SphI—Sph I fragment (X).

By means of suitable experiments described hereinbelow it has been found that the DNA (I) shown in FIG. 1 comprises a sequence encoding CAS activity.

Accordingly, in another aspect, the present invention provides DNA comprising a gene encoding a protein with clavaminic acid synthase activity.

The gene for CAS activity is located within the DNA fragment (IX) shown in FIG. 4, and accordingly, DNA fragment (IX) is another preferred subfragment according to the invention.

It will be understood that the invention encompasses DNA which may not have the precise configuration of restriction sites illustrated in FIGS. 1 to 4 if the said DNA has been derived by standard techniques including nucleotide deletion, substitution, addition or inversion from the DNA according to any aspect of the invention described above.

Preferably the DNA of this invention is derived from *S. clavuligerus* ATCC 27064 and FIGS. 1 to 4 show *S. clavuligerus* DNA.

However the invention also encompasses DNA sequences obtained from suitable clavulanic acid producing organisms other than *S. clavuligerus*, which sequences do not have the configuration of restriction sites illustrated in FIGS. 1–4 but which hybridise, preferably under conditions of high stringency, with the DNA (III) shown in FIG. 3, or a subfragment thereof, and which code for an enzyme involved in clavulanic acid biosynthesis.

Other know clavulanic acid producing organisms include S. jumonjinensis ATCC 29864 and S. katsurahamanus T-272.

In a further aspect the invention provides recombinant DNA comprising the DNA of any aspect of the invention as hereinabove described.

Preferably the recombinant DNA of the invention comprises a recombinant vector, more preferably a vector capable of transforming and undergoing autonomous replication in a clavulanic-acid producing organism or a vector from which insert DNA can be integrated into the chromosome of the clavulanic acid producing organism via homologous recombination.

In one preferred aspect the recombinant vector is a high expression vector.

The DNA according to any aspect of this invention may be introduced into any suitable vector by methods well known in the art, for example by direct combination of cohesive ends, homopolymer tailing, or by means of a linker or adaptor molecule.

In one preferred aspect, the vector is derived from a Streptomycete.

Specific examples of such vectors include the following
(1) pIJ 913 (molecular weight 15.7 megadaltons), a low copy number vector described in Lydiate, D. J., et al., Gene (1985), 35, 223–235;
(2) pIJ 702 (molecular weight 3.7 megadaltons), a high copy number vector described in Katz, E. et al, J. Gen. Microbiol (1983), 129, 2703–2714.
(3) pIJ 680 described by Hopwood et al (1985) Genetic Manipulation of Streptomyces. A Laboratory Manual. The John Innes Foundation.

The vector may also be derived from a non-Streptomycete; for example the cosmid pTCF (Grosveld et al., Nucleic Acids Research, 1982, 10, 6715–6732) or the plasmid pAT 153 (Twigg, A. J. and Sherratt, D., Nature, 1980, 283, 216–218).

It will be appreciated that recombinant vectors prepared according to the above methods may contain the insert DNA in one of two possible orientations. Recombinant vectors containing both orientations are included within the scope of the invention. Thus, for example, when the insert DNA fragment has the configuration of restriction sites shown in (IV) (FIG. 4) and the plasmid vector into which it is introduced is pIJ 913, the restriction maps of the resulting recombinant plasmids, referred to as pBROC 41A and pBROC 41B, are shown in FIGS. 5(a) and 5(b). Of these plasmids, pBROC 41B [FIG. 5(b)] is preferred.

A preferred recombinant vector which may be prepared by inserting the DNA (III) is FIG. 3 into pAT 153 is shown in FIG. 6 and is designated pBROC 31.

Other preferred recombinant vectors according to the invention include those designated pWOR10 (constructed by ligating DNA fragment IX as hereinabove defined into the Bam HI site of pIJ680) and pBROC44 (constructed by ligating the same DNA fragment IX into the Bgl II site of pIJ702). In pWOR10 the unique Bcl I site in fragment IX is 2.45 Kb from the unique Xho I site in the pIJ 680 vector. In pBROC44 the unique Bcl I site in fragment IX is 3 Kb from the unique Bam HI site of the pIJ 702 vector.

The insert DNA in one vector may be sub-cloned into another vector by standard procedures. For example, the recombinant plasmid pBROC 41B characterized as shown in FIG. 5(b), may be obtained by:

a) isolating the large Eco RI—Eco RI segment (14.35 Kb) from pBROC 31 (FIG. 6) by cleavage with Eco RI; and
b) litigating the above Eco RI—Eco RI segment to pIJ 913, linearized by cleavage with Eco RI.

To prepare the DNA and recombinant vectors of the invention, a random array of chromosomal DNA fragments may be generated by partial digestion of S. clavuligerus (ATCC 27064) DNA by any convenient restriction enzyme. The endonuclease Mbo I and its isoschizomers may be particularly suitable for this purpose The DNA fragments may then be size-fractionated on a salt gradient and fractions containing fragments around 35–45 Kb in length may be taken (see Grosveld et al, Nucleic Acids Research, 1982, 10, 6715–6732). The DNA fragments may then be ligated by conventional 'shot-gun' methods to a cleaved vector to form a 'clone bank'.

If desired, smaller fragments, for example of length 10 Kb or more, may be obtained by size fractionation on an agarose gel using electrophoretic elution. These smaller DNA fragments may then be used to form a clone bank as described above.

The vector used to form the clone bank may be a cosmid (able to carry large pieces of DNA), and for this purpose the cosmid pTCF (see Grosveld et al, loc. cit.) is particularly suitable.

The plasmid pAT 153 may also advantageously be used in forming a clone bank to carry smaller pieces of DNA.

A clone bank prepared as described above may then be 'probed' by conventional methods using as a hybridization probe a piece of DNA capable, when inserted into a suitable vector and transformed into a non-producer mutant strain of a clavulanic acid-producing host (a 'blocked' mutant) of restoring the ability of the host to synthesize clavulanic acid. It will be appreciated that the probe will be radiolabeled, for example with $^{32}$P, and may either comprise the said piece of DNA itself or consist of a vector containing the said DNA provided that the said vector has no appreciable homology with the vector used to form the clone bank to be probed.

Suitable probes may be isolated by the procedure described by C. R. Bailey et al. in Biotechnology, 1984, 2, 808–811.

A preferred probe is the plasmid pWOR1 described by C. R. Bailey et al. (loc. cit.).

To carry out the procedure described in Biotechnology, 1984, 2, 808–811, it is necessary to have access to S. clavuligerus dc1C8, a mutant strain of S. clavuligerus which lacks the ability to produce clavulanic acid. The details relating to the deposition, derivation and characteristics of S. clavuligerus dc1C8 are as follows.

Deposition

The strain S. clavuligerus dc1C8 was deposited in the National Collection of Industrial and Marine Bacteria, Aberdeen, Scotland on Feb. 19, 1986, the deposit (accession number NCIB 12209) being made under the terms of the Budapest Treaty on the International Recognition of the Deposit of Micro-organisms for the Purpose of Patent Procedure.

Derivation of S. clavuligerus NCIB 12209

Breaking out a sample of S. clavuligerus ATCC 27064 shows a variety of morphologies. Fourteen different types were recognised. One of these isolated as S. clavuligerus SC2.

Treatment of S. clavuligerus SC-2 with 10 $\mu$M of ethidium bromide was then carried out on petri dishes and the plates were incubated for 10 days. Survivors were assayed for clavulanic acid production. One isolate which produced no detectable clavulanic acid when assayed by HPLC (detection at 230 mm) was designated as strain dc1C8 and deposited under accession number NCIB 12209 as hereinabove described.

S. clavuligerus NCIB 12209 forms a further aspect of the present invention.

Taxonomy of S. clavuligerus NCIB 12209

The taxonomical and morphological properties of S. clavuligerus NCIB 12209 were found to be essentially similar to those of S. clavuligerus ATCC 27064, a description of which may be found in U.S. Pat. No. 3,862,008 and also in Higgnes, C. E. and Kastner, R. E., Int. J. Systematic Bacteriol., 1971, 21, 326–331.

After probing a clone bank prepared as described above with a suitable hybridization probe, for example pWOR1, insert DNA corresponding to, or embracing, the DNA of the invention may then be sub-cloned by standard methods, or cleaved as hereinbefore described.

In the event that an inappropriate or too short piece of DNA is obtained form the probing step, the newly isolated DNA fragment may itself be used as a hybridization probe (after radio-labelling by conventional methods, e.g. nick-translation) to identify further positive colonies in the clone bank, the insert DNA of which may be analysed by restriction mapping and if necessary, modified by cleavage with appropriate restriction enzymes.

The above process may be repeated until the required DNA according to the invention is isolated.

In yet a further aspect the invention provides a host transformed by a recombinant vector of the invention.

The host may be transformed by standard techniques.

In one aspect the host may be a non-producer of clavulanic acid, for example E. coli or S. lividans. Such hosts may be of value in genetic manipulation procedures and can be advantageously used to express large quantities of enzymes involved in clavulanic acid biosynthesis, for example an enzyme having CAS activity.

Preferred hosts, however, are those which are natural producers of clavulanic acid when cultured in an appropriate medium, or non-producing mutants thereof blocked in clavulanic acid biosynthesis which the DNA according to the invention can then repair so that clavulanic acid synthesis is restored and preferably enhanced. Preferred hosts of this type are Streptomycetes including S. clavuligerus ATCC 27064, S. jumonjinensis ATCC 29864 and S. katsurahamanus T-272 or are derived therefrom.

The advantage of employing such hosts is that under appropriate conditions an increased titre of clavulanic acid can be obtained after transformation with a recombinant vector according to the invention.

Accordingly the present invention further provides a method for producing clavulanic acid in a host which is naturally a producer of clavulanic acid or from a blocked non-producing mutant of a said host, which method comprises the steps of:

(a) transforming the said host or said non-producing mutant thereof with a recombinant vector according to the invention; and (b) culturing the transformants so formed under appropriate conditions so that production of clavulanic acid takes place.

General methods for culturing a clavulanic acid-producing organism so as to obtain clavulanic acid are given in U.K. Patent Specification No. 1,508,977.

In the above method the host is preferably S. clavuligerus ATCC 27064, or is derived therefrom.

Preferably the recombinant vector used in the above method is pWOR10 as hereinabove defined.

The following examples illustrate the invention.

EXAMPLE 1

Construction of a Library of S. clavuligerus ATCC 27064 DNA in the Cosmid Vector pTCF S. clavuligerus ATCC 27064 chromosomal DNA was isolated as described in European Patent Application Publication No. 0 233 715. Three aliquots of 20 µg of chromosomal DNA were partially digested with Mbo I (0.5 units per µg of DNA) for 5 minutes, 10 minutes and 15 minutes under standard conditions. The three aliquots were pooled and fractionated on a salt (1.25M–5M NaCl)/Tris EDTA gradient and centrifuged for 3 hours at 39K rpm in a SW40.1 Beckman rotor. Twelve fractions were collected and the isolated DNAs from fractions 5–9 yielded 10 µg Mbo I DNA fragments around 35–45 kb in size.

The preparation of pTCF vector arms was carried out according to Grosveld, F. G., Lund, T., Murray, E. J., Mellor, A. L., Dahl, H. H., Flavell, R. A., Nucleic Acids Research (1982), 10, 6715–6732.

S. clavuligerus DNA fragments and vector arms were ligated in a ratio of 5:3:3, the mix packaged and used in the transduction of E. coli ED8767 as described in Grosveld et al. (loc. cit.). This procedure gave $4 \times 10^6$ colonies per µg packaged DNA.

EXAMPLE 2

Preparation of DNA I

5000 E. coli ED8767 colonies containing pTCF with S. clavuligerus ATCC 27064 DNA inserts were immobilised and lysed on nitrocellulose filters. The plasmid pWOR1 (Bailey, C. R. et al. (loc. cit,) was isolated, nick translated and used to probe the filters by standard colony hybridisation techniques.

Two hydridising colonies were obtained which, when combined, contain the 60 kb DNA I segment illustrated in FIG. 1.

EXAMPLE 3

Construction of a Library of S. clavuligerus ATCC 27064 DNA in pAT153

S. clavuligerus ATCC 27064 chromosomal DNA was isolated as described in European Patent Application Publication 0 233 715.

60 µg of S. clavuligerus ATCC 27064 DNA was partially digested with Mbo I and fractionated on an agarose gel. DNA was isolated from fractions containing fragments of >10 kb in size by electrophoretic elution as described by Maniatis, T., Fritsch, E. F., Sambrook, J. (1982) Molecular Cloning: A Laboratory Manual (Cold Spring harbor Laboratory).

10 µg of pAT153 (Twigg and Sherratt (loc. cit.)) was digested with Bam HI and treated with calf intestinal alkaline phosphatase to remove terminal phosphate groups and prevent recircularisation. The vector and >10 kb fragments of S. clavuligerus ATCC 27064 DNA were linked together and used to transform E. coli DH1.

EXAMPLE 4

Preparation of DNA III

6000 E. coli DH1 colonies containing pAT153 with S. clavuligerus ATCC 27064 inserts were immobilised and lysed on nitrocellulose filters. The 2.2 kb Sph I—Bgl II insert fragment from pWOR1 [sites 3–4 in FIG. 3 of Bailey et al (loc. cit.)] was isolated, nick translated and used to probe the filters by standard colony hybridisation techniques.

One hybridising colony was obtained which contains the 13.1 kb DNA III fragment illustrated in FIG. 3.

EXAMPLE 5
Enhancement of Clavulanic Acid Titre in *S. clavuligerus* Strain SC2 by the Plasmid pWOR10

Plasmid pWOR10 was constructed by ligating the Bgl II-Bgl II fragment IX (FIG. 4) into the Bam HI site of pIJ680 (Hopwood et al., 1985 Genetic Manipulation of Streptomyces. A Laboratory Manual. The John Innes Foundation).

Plasmid pWOR10 was transformed into *S. clavuligerus* SC2 (reisolate of wild type) by a method analogous to that described in C. R. Bailey et al (loc cit.). Transformants were picked off and restreaked on M5D medium (Dextrin, 1.0%; $K_2HPO_4$, 0.1%; $MgSO_4$, 0.1%; NaCl, 0.1%; $(NH4)_2$ $SO_4$, 0.1%; CaCO3, 0.4%; Trace Elements ($FeSO_4$ 0.0001%; $MnCl_2$, 0.0001%; ZnSO4, 0.0001%,; Agar, 2.0%) containing 5 µg/ml thiostrepton. Cells of each transformant were stabbed onto M5D and grown for 6 days at 26° C.

The bioassay plates were then overpoured with soft blood agar (Oxoid) containing *Klebsiella aerogenes* strain as described in Reading, C. and Cole, M. (1977) Antimicrob. Agents Chemother, 11, 852–857, 4% tetrazolium salts and 5 µg/ml penicillin G. After overnight incubation at 26° C. zones of inhibition were measured. Those transformants showing zones greater than the control culture were transferred to shake-flask culture for accurate titre assessment. Cells are inoculated into 25 ml of a suitable seed medium as described in U.K. Patent Specification No. 1,508,977 and grown for 3 days at 26° C. with shaking. 1 ml of seed culture is inoculated into a final stage medium as described in U.K. Patent Specification No. 1,508,977 and grown at 26° C. for four days.

Samples of culture broth were withdrawn after three and four days growth and assayed for clavulanic acid productivity as described in Bird, A. E. et al (1982) Analyst, 107, 1241–1245 and Foulston M., and Reading, C. (1982) Antimicrob Agents Chemother., 22, 753–762.

Results

Of the 21 isolates tested, one gave enhanced titres compared to *S. clavuligerus* SC2 yielding up to 53% advantage in cultures grown in the absence of thiostrepton and 39% advantage in cultures grown in the presence of thiostrepton. In all cases autonomous pWOR10 was found to be present.

EXAMPLE 6
Transformation of *S. lividans* with pBROC44 pBROC 44 was prepared by ligating the Bgl II-Bgl II fragment IX (FIG. 4) in to the Bgl II site of pIJ 702 (see Hopwood et al. loc. cit.)

*S. lividans* spores were inoculated into 25 ml of protoplast seed medium (tryptone soya broth+1% maltose) in a 250 ml shake flask and incubated for 3 days at 30° C. with shaking. 1 ml of seed culture was transferred to 25 ml final stage protoplasting medium [comprising 15 ml YEME (Hopwood et al., loc. cit) with 1% maltose plus 10 ml TSB plus 0.5% glycine plus 1% maltose] in 250 ml shake flask containing a coiled spring. Incubation was overnight (16 h) at 30° C. The culture was harvested in sterile centrifuge tubes and mycelium washed in 10.3% sucrose. The cell pellet was resuspended in 1.5 ml lysozyme mix and incubated at 25° C. for 1 hour, mixing occasionally. Protoplast formation was monitored using a microscope. Protoplast buffer (PB) (4 ml) (Hopwood et al., loc. cit.) was added and mixed and the cell suspension was then filtered through sterile cotton wool filters. The protoplast suspension was centrifuged, washed briefly in PB and finally resuspended in 2 ml PB. Protoplast concentration was measured using a Thoma counting chamber.

$4 \times 10^9$ protoplasts were placed in fresh centrifuge tube, 5 ml of PB added and pelleted by centrifugation. Protoplasts were resuspended in approx. 400 µl of PB. 5 µl of ligation mix was added to the protoplast suspension and within 30 seconds 0.5 ml transformation buffer (Hopwood et al. loc. cit., page 246) was added.

After 10 seconds 5 ml of PB was added and the protoplasts were centrifuged.

Protoplasts were resuspended in 1 ml PB and dilutions made in PB down to $10^{-5}$. 0.1 ml samples of each dilution were plated out onto regeneration medium R2YE; see Thompson, C. J., Ward, J. M. and Hopwood, D. A. (1980) Nature, 286, 525–527. Agar plates were incubated at 30° C. After 20 hours plates were overpoured with 2 ml soft nutrient agar containing 500 µg/ml thiostrepton. Agar plates were incubated for a further 3 days. Thiostrepton resistant transformants were picked off regeneration plates and restreaked on fresh R2YE agar. After 3–4 days growth transformants were inoculated into seed medium containing 50 µg/ml thiostrepton and grown with shaking for 2 days at 30° C. Plasmid was isolated according to the method of Hopwood et al (loc. cit). The correct construct designated pBROC44 was confirmed by restriction endonuclease digestion as described by Maniatis et al (loc. cit) (1982).

EXAMPLE 7
The Demonstration of Clavaminic Acid Synthase Activity in pBROC44-Transformed *S. lividans*

The experiments described below demonstrate the presence of clavaminic acid synthase (CAS) activity in *S. lividans* that had been transformed by pBROC44 (Example 6). Three cultures were examined:

(i) *S. lividans* host;
(ii) *S. lividans* containing pIJ702, and
(iii) *S. lividans* containing pBROC44 (Example 6).

Cultures (i) and (ii) acted as negative controls for (iii).

Because the vector pIJ702 contains a locus for thiostrepton resistance, the two cultures containing this vector were grown in the presence of thiostrepton (50 µg/ml). The host itself was grown without thiostrepton.

The medium used was a follows:

| | | |
|---|---|---|
| Difco yeast extract | 3 g) | |
| Difco bacto peptone | 3 g) | |
| Oxoid malt extract | 3 g) | 1 litre $H_2O$ |
| Glucose | 10 g) | |
| Sucrose | 340 g) | | and was supplemented after autoclaving with $MgCl_2$ and glycine to final concentrations of 5 mM and 50 mM, respectively.

The medium was inoculated with a single agar plug from a spore plate, and cultures were grown in 250 ml or 500 ml sprung shake-flasks at 31° C.

The mycelium was harvested by centrifugation after 48 hr. growth, and was sonicated (3×5 sec. bursts) to release intracellular enzymes in the same volume of 50 mM TRIS HCl/10 mM $MgCl_2$/10 mM KCl/10% glycerol/1 mM phenylmethylsulphonyl fluoride (PMSF)/pH 7.5.

To assay for CAS activity, the centrifuged sonicate (115 µl) was incubated with $Fe^{2+}$(15 µl, 10 mM), α-ketoglutarate (15 μl, 10 mM) and the substrate for CAS [5-amino-3-hydroxy-2-(2-oxoazetidin-1-yl)valerate; proclavaminic acid; as described in EP-A-O 213 914] (5 μl, 5 mg/ml) for 5 minutes at room temperature, followed by incubation with imidazole (37.5 μl, 20%, pH 6.8) for 10 minutes, then detection of the derivatised product by HPLC using a 30 cm Waters C18 column equilibriated in 0.1M $NaH_2PO_4$/6% MeOH/pH 3.2 at 2 mls/min., detecting at 312 nm. Soft gel permeation chromatography was performed at 4° C. using a 2.6×45 cm column of Ultrogel AcA 54 equilibrated in sonication buffer (see above) at 20 mls/hr. Fractions were assayed for CAS activity as above. Protein assays were performed according to the method of Bradford (1976) Analytical Biochem. 72, 248–254.

Results

Cultures of S. lividans alone, S. lividans containing the vector pIJ702, and S. lividans transformed with pBROC44 were grown for 48 hours to give an opaque broth. The mycelium of each culture was harvested and sonicated, and the centrifuged sonicates were assayed for CAS activity. HPLC data showed that the S. lividans transformed with pBROC44 gave rise to an HPLC peak with the following characteristics:

(i) it co-elutes (2.5 mins) with the standard for clavaminic acid.

(ii) it is absent from the two control cultures (S. lividans alone and S. lividans containing pIJ702 without the insert);

(iii) it is absent when the pBROC44-transformed culture is assayed in the absence of either $Fe^{2+}$, α-ketoglutarate or the substrate.

This evidence shows that the pBROC44-transformed culture gives rise to CAS activity.

The specific activity of the cAS purified from S. lividans/pBROC44 was found to be 0.0036 μmole/min/mg protein. This compares with values between 0.008 and 0.06 μmole/min/mg protein for CAS from S. clavuligerus ATCC 27064 (reisolate SC2). Although the specific activity of the cloned CAS is slightly less than that of native CAS, the data indicate that the enzyme is translated intact, and the pBROC44 contains the complete CAS gene.

We claim:

1. Strain NCIB 12209.

2. A purified and isolated DNA encoding a protein with clavaminic acid synthase activity, said DNA having a portion that hybridizes to the DNA fragment (IX) shown in FIG. 4, said DNA fragment (IX) derived from S. clavuligerus.

3. A recombinant DNA comprising the DNA of claim 2.

4. A recombinant vector comprising the recombinant DNA of claim 3.

5. A host transformed with the vector of claim 4.

6. The transformed host of claim 5, wherein the host is selected from the group consisting of S. clavuligerus ATCC 27064, S. jumonjinensis ATCC 29864, S. katsurahamanus T-272, and mutants thereof.

7. The purified and isolated DNA according to claim 2 which is derived from S. clavuligerus.

8. A recombinant DNA comprising the DNA of claim 7.

9. A recombinant vector comprising the recombinant DNA of claim 8.

10. A host transformed with the vector of claim 9.

11. The transformed host of claim 10, wherein the host is selected from the group consisting of S. clavuligerus ATCC 27064, S. jumonjinensis ATCC 29864, S. katsurahamanus T-272, and mutants thereof.

12. A purified and isolated DNA encoding a protein with clavaminic acid synthase activity, said DNA comprising DNA fragment (IX) shown in FIG. 4, said DNA fragment (IX) being derived from S. clavuligerus.

13. A recombinant DNA comprising the DNA of claim 12.

14. A recombinant vector comprising the recombinant DNA of claim 13.

15. A host transformed with the vector of claim 14.

16. The transformed host of claim 15, wherein the host is selected from the group consisting of S. clavuligerus ATCC 27064, S. jumonjinensis ATCC 29864, S. katsurahamanus T-272, and mutants thereof.

17. The purified and isolated DNA according to claim 12 which is derived from S. clavuligerus.

18. A recombinant DNA comprising the DNA of claim 17.

19. A recombinant vector comprising the recombinant DNA of claim 18.

20. A host transformed with the vector of claim 19.

21. The transformed host of claim 20, wherein the host is selected from the group consisting of S. clavuligerus ATCC 27064, S. jumonjinensis ATCC 29864, S. katsurahamanus T-272, and mutants thereof.

22. A method for identifying a DNA involved in clavulanic acid biosynthesis using the clavulanic acid non-producing mutant S. clavuligerus strain NCIB 12209, said method comprising the steps of:

(a) transforming into NCIB 12209 a library of DNA fragments from a wild-type strain of S. clavuligerus;

(b) testing the transformed NCIB 12209 for the ability to produce clavulanic acid; and (c) isolating the transformed DNA from the NCIB 12209 clavulanic acid producers.

23. A method for enhancing the production of clavulanic acid in a clavulanic acid producing strain of S. clavuligerus comprising:

(a) introducing the transformed DNA of claim 22 into an expression vector;

(b) transforming said expression vector into a S. clavuligerus host;

(c) culturing said host under conditions effective for the production of clavulanic acid; and (d) recovering the clavulanic acid produced thereby.

* * * * *